United States Patent [19]

Minagawa

[11] Patent Number: 4,846,795
[45] Date of Patent: Jul. 11, 1989

[54] BLOOD BAG SYSTEM

[75] Inventor: Yoshinori Minagawa, Fujinomiya, Japan

[73] Assignee: Terumo Kabushiki Kaisha, Tokyo, Japan

[21] Appl. No.: 283,007

[22] Filed: Dec. 8, 1988

Related U.S. Application Data

[63] Continuation of Ser. No. 142,300, Jan. 11, 1988, abandoned, which is a continuation of Ser. No. 42,595, Apr. 23, 1987, abandoned, which is a continuation of Ser. No. 914,557, Oct. 2, 1986, abandoned, which is a continuation of Ser. No. 844,266, Mar. 25, 1986, abandoned, which is a continuation of Ser. No. 596,538, Apr. 4, 1984, abandoned.

[30] Foreign Application Priority Data

Jun. 27, 1983 [JP] Japan ............................. 58-98021[U]

[51] Int. Cl.⁴ ............................................. A61M 5/00
[52] U.S. Cl. .................................. 604/410; 604/244; 604/4
[58] Field of Search ........................................ 604/4-6, 604/244, 408, 410, 262

[56] References Cited

U.S. PATENT DOCUMENTS 3,187,750 6/1965 Tenczar, Jr. .
3,648,693 3/1972 Koremura .
3,945,380 3/1976 Dabney et al. .
4,181,140 1/1980 Bayham et al. .
4,195,632 4/1980 Parker et al. .
4,197,847 4/1980 Djerassi .
4,386,622 6/1983 Munsch ............................. 604/244
4,407,660 10/1983 Nevens et al. ..................... 604/6
4,435,179 3/1984 Walker .............................. 604/244

FOREIGN PATENT DOCUMENTS 0011144 5/1980 European Pat. Off. .
0057001 8/1982 European Pat. Off. .
0073847 3/1983 European Pat. Off. .
8300813 3/1983 Int'l Pat. Institute .
WO/8101105 4/1981 PCT Int'l Appl. .

Primary Examiner—C. Fred Rosenbaum
Assistant Examiner—Denise Whelton
Attorney, Agent, or Firm—Frishauf, Holtz, Goodman & Woodward

[57] ABSTRACT

In a blood bag system for plasma transfusion and cell return including two or more blood bags containing anticoagulant and connected to a puncture needle through two or more branch tubes and a common main tube, a cell return port is connected to the branch and a breakable flow path closure is inserted in one branch tube adjacent the branch. When broken, the flow path closure allows fluid communication through the branch tube. Blood is first collected in the first blood bag, which bag is sealed when filled and separated from the system. Then, the flow path closure is manually broken to permit blood collection into the second blood bag.

14 Claims, 2 Drawing Sheets

BLOOD BAG SYSTEM

This application is a continuation of Ser. No. 142,300 filed Jan. 11, 1988; which is a continuation of Ser. No. 042,595 filed Apr. 23, 1987; which is a continuation of Ser. No. 914,557 filed Oct. 1986; which is a continuation of Ser. No. 844,266 filed Mar. 25, 1986; which is a continuation of Ser. No. 596,538 filed Apr. 4, 1984 all now abandoned.

BACKGROUND OF THE INVENTION

1. Field of the Invention

This invention relates to a blood bag system, and more particularly, to a blood bag system capable of transfusing a necessary component (e.g. plasma) and returning the remaining component (e.g. corpuscle or cell) of blood to the donor.

2. Description of Prior Art

Prior art blood bag systems will be discussed with reference to the drawings.

Referring to FIG. 1, there is diagrammatically illustrated a typical blood bag system according to the prior art. The blood bag system 1 comprises first and second blood bags 2A and 2B each having an inlet 3 for collecting blood, an outlet 4 for transfusing a plasma component, and another outlet 5 for transfusing a cell or corpuscle component of blood, and containing a given volume of an anticoagulant previously injected therein. First and second sections of tubing 6A and 6B are connected at one end to the inlets 3 of the blood bags 2A and 2B, and at the other end collectively to one end of a main section of tubing 8 via a branch pipe 7. A hypodermic needle 9 for collecting blood is connected to the other end of the main section of tubing 8. Cell return means 11 is connected to one of the collecting sections of tubing, 6B in the illustrated embodiment, via a branch pipe 10.

To carry out plasma transfusion, the blood bag system 1 may be operated as follows. The needle 9 is inserted into the donor's vein and blood is collected in the first blood bag 2A. Thereafter the first blood bag 2A is disconnected from the first section of tubing 6A, and placed in a centrifuge to separate the blood into plasma and cell components. The thus separated plasma component is transfused from the bag 2A to the patient through the plasma outlet 4 while the separated cell component is returned or transfused back from the bag 2A to the donor through the cell outlet 5, return means 11, and needle 9. The procedures of blood collection, separation, transfusion, and return are repeated for the second blood bag 2B. With this blood bag system, a necessary amount of plasma can be collected by repeating the procedures of blood collection, transfusion and return without unnecessarily increasing the volume of blood taken out of the donor in each collecting process. Furthermore, the need for inserting the puncture needle into the donor's vein for every blood collecting process is eliminated to minimize the damage to the vascular wall and the pain to the donor by puncture.

In the above-illustrated blood bag system 1, for the purpose of preventing the anticoagulant in each of the blood bags 2A and 2B from being transferred to the other blood bag during autoclave sterilization as well as for the purpose of ensuring that the blood collected in each of the blood bags 2A and 2B be kept anticoagulant, the blood collecting inlet 3 of one of the blood bags, for example, blood bag 2B is removably fitted with a spherical bead 12 to block the flow path of the inlet 3.

However, in the manufacture of the blood bag system 1, the step of mounting the bead 12 at the blood collecting inlet 3 of the second blood bag 2B is complicated and troublesome. When blood is to be collected in the second blood bag 2B, the bead 12 must be removed from the inlet 3 and dropped into the bag 2B. Not only the step of removal of the bead 12 is cumbersome, but the periphery of the inlet 3 might be damaged or fractured by the nail or the like. Moreover, during the centrifugal separation after blood collection, the bead 12 in the second blood bag 2B might be centrifugally forced against the inner wall of the bag with possible fracture. When the bead 12 is mounted only at the inlet 3 of the second blood bag 2B, the anticoagulant contained in the first blood bag 2A will flow into all the flow paths of the sections of tubing 6A and 6B and the main section of tubing 8 to wet the tube inner surface By this reason, the volume of anticoagulant contained in the first blood bag 2A must be somewhat larger than that in the second blood bag 2B, further complicating the manufacture process. In addition, since the flow paths to be wetted by the anticoagulant contained in the first blood bag 2A total to a considerable length, it becomes difficult to previously distribute the anticoagulant properly throughout the flow paths because of flow resistance and other factors.

FIG. 2 diagrammatically illustrates another prior art blood bag system as disclosed in Nevens et al., U.S. Pat. No. 4,407,660. This blood bag system 13 is similar to the blood bag system 1, but different from the previous system in that it uses a plug 14 capable of blocking and allowing communication through both the connection between the second section of tubing 6B and the main section of tubing 8 and the connection between the cell return means 11 and the main section of tubing 8.

In this blood bag system, when the plug 14 blocks communication through the connection between the second section of tubing 6B and the main section of tubing 8, the anticoagulant contained in the first blood bag 2A wets the first section of tubing 6A and the main section of tubing 8 and the anticoagulant in the second blood bag 2B wets the second section of tubing 6B. It is thus possible to substantially equalize the volumes of anticoagulant contained in the blood bags 2A and 2B and to cause the anticoagulant to be properly or uniformly distributed throughout the flow paths because the flow paths to be wetted are individually assigned to the respective anticoagulant fractions in the bags.

The above-described blood bag system, however, requires careful operation of withdrawing the plug 14 halfway to communicate the second section of tubing 6B with the main section of tubing 8 when blood is to be collected in the second blood bag 2B. Care must be taken so as not to fully remove the plug 14 from the cell return means 11. Further, when the cell transfusion outlet 5 of each of the blood bags 2A and 2B is connected to the cell return means 11, the plug 14 must be fully withdrawn from the cell return portion 11, with the possible entry of bacteria from the atmosphere into the main section of tubing 8.

SUMMARY OF THE INVENTION

It is, therefore, an object of the present invention to provide an improved blood bag system including a plurality of blood bags connected to a main section of tubing through a corresponding plurality of sections of tubing, wherein substantially equal volumes of anticoagulant may be contained in the blood bags to ensure that the anticoagulant be properly and uniformly distributed throughout the sections of tubing and main section of tubing.

It is another object of the present invention to provide a blood bag system which is efficient to manufacture, easy to operate and safe in service.

The present invention is directed to a blood bag system comprising a plurality of blood bags each having an inlet for blood collection and an outlet for blood transfusion and containing a given volume of an anticoagulant therein, a corresponding plurality of sections of tubing for blood transfer each having one end connected to the inlet of one blood bag, and a main section of tubing having one end connected to the other ends of the sections of tubing in common. A needle is connected to the other end of said main section of tubing for collecting blood. Return means is connected to the main section of tubing or any one of the sections of tubing for returning a cell component of blood to the donor.

According to a first aspect of the present invention, provided that N is the number of blood bags in the system, flow path control means is positioned in each of sections of tubing corresponding to at least (N−1) blood bags at a point near to the main section of tubing, but on the side of the blood bag with respect to said return means. The control means normally blocks communication through the corresponding section of tubing, but when broken, allows communication through the section of tubing.

In a preferred embodiment of the present invention, the flow path control means comprises an annular base disposed in and sealed to the inner surface of the section of tubing and defining a flow path therethrough. A breakable plug member is integrally connected to that end of the base which is positioned on the side of the blood bag, to block the flow path of the base. The plug member is breakable from the base to open the flow path.

Preferably, the plug member is a conical plug having the bottom breakably connected to the annular base. Alternatively, the plug member has a flat tip or is truncated. That portion of the section of tubing which encloses the flow path control means has a larger diameter than the remaining portion. The outer diameter of the flow path control means is selected to be larger than the inner diameter of the remaining portion of the section of tubing.

Preferably, the return means is connected to the main section of tubing through a branch pipe while one end of the main section of tubing is connected to the other ends of tubing through the same branch pipe. The return means consists of a short section of tubing closed with a plug of a material puncturable with a hypodermic needle.

BRIEF DESCRIPTION OF THE DRAWINGS

The above and other objects, features and advantages of the present invention will be more fully understood by reading the following description taken in conjunction with the accompanying drawings, in which.

DESCRIPTION OF THE PREFERRED EMBODIMENTS

Figure 1:
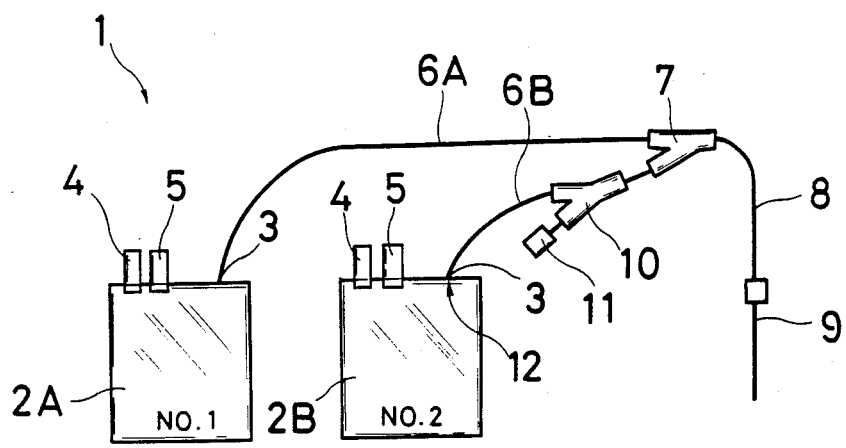
FIG. 1 illustrates a prior art blood bag system.
Figure 2:
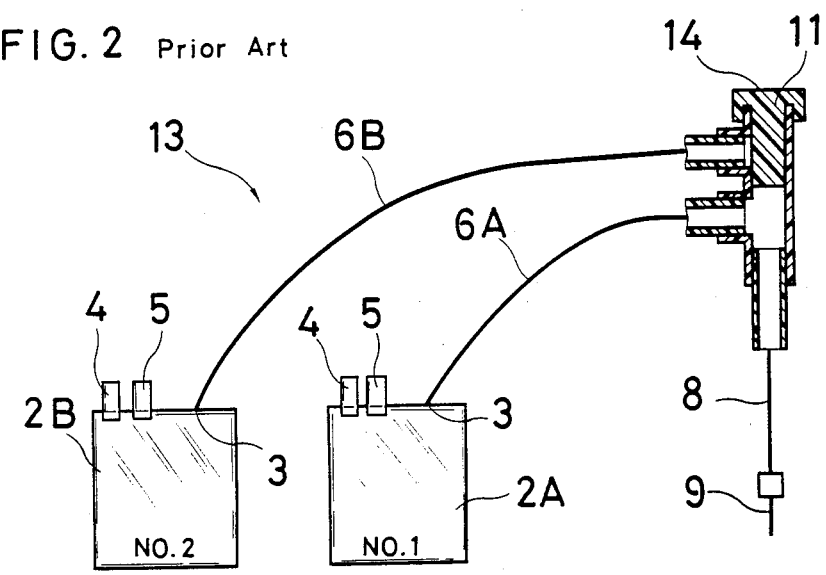
FIG. 2 illustrates another prior art blood bag system.
Figure 3:
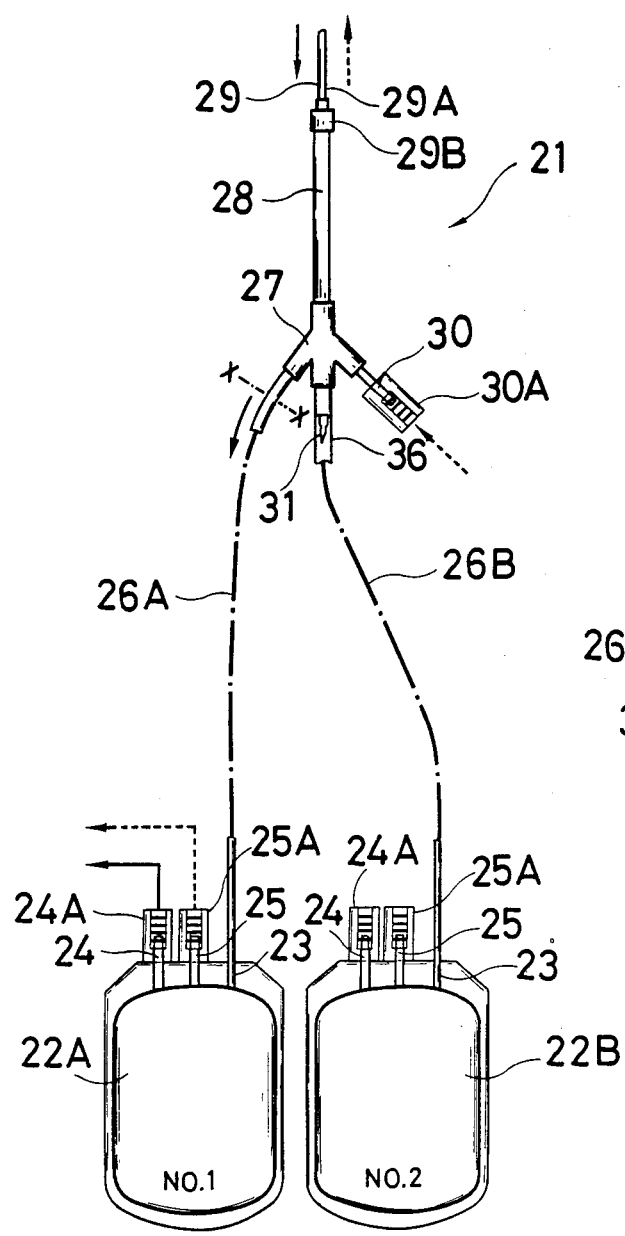
FIG. 3 illustrates one embodiment of the blood bag system according to the present invention.

FIG. 3 diagrammatically shows one embodiment of a blood bag system 2 of the present invention. The blood bag system 21 includes first and second blood bags 22A and 22B in which an anticoagulant is previously admitted in a sufficient amount corresponding to the volume of blood to be contained in the bag to prevent coagulation of blood to be collected therein. Each of the blood bags 22A and 22B is provided with an inlet 23 for collecting blood, an outlet 24 for transfusing blood plasma, and another outlet 25 for transfusing blood cells. The first and second sections of tubing 26A and 26B are connected at one end to the blood bags 22A and 22B, respectively, and at the other end collectively to one end of a main section of tubing 28 via a branch pipe 27. A needle 29 for collecting blood is connected to the other end of the main section of tubing 28. Cell return means 30 is connected to the main section of tubing 28 via the branch pipe 27. The cell return means 30 in the form of a short section of tubing is fitted with a plug formed of a material puncturable with a hypodermic needle, for example, a rubber plug. Although the cell return means 30 may be located intermediate each of the sections of tubing 26A and 26B, it is preferably connected directly to the main section of tubing 28 as illustrated in order to minimize the length of a path for back transfusion. In the illustrated embodiment, a protector 29A is fluid-tightly engaged with a hub 29B on the needle 29 for the purpose of preventing leakage of anticoagulant in the first blood bag 22A. Furthermore, the plasma outlet 24, cell outlet and cell return means 30 are covered with caps 24A, 25A and 30 A, respectively.

At that position in the second section of tubing 26B which is located near to the main section of tubing 28 (but on the side of the blood bag 22B with respect to the cell return means if the cell return means 30 is connected to the second section of tubing 26B), is provided flow path control means 31 which blocks communication through the second section of tubing 26 B in normal or unbroken conditions, but allows communication through the second section of tubing 26B when broken.

Figure 4:
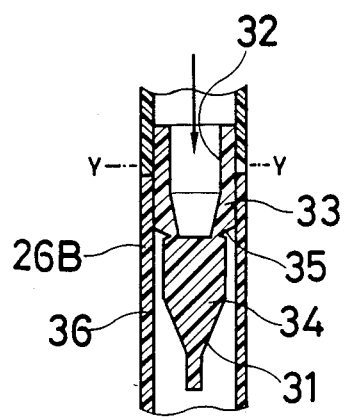
FIG. 4 is an enlarged cross section of the flow path control means inserted in the blood bag system shown in FIG. 3.

As best shown in FIG. 4, the flow path control means 31 comprises an annular base in the form of a sleeve member 33 joined to the inner surface of the section of tubing 26B by adhesion or heat welding and defining a flow path 32 therein. A breakable plug member 34 is integrally connected to that end of the sleeve member 33 which is positioned on the side of the blood bag, to block or close the flow path 32 of the sleeve member 33. The plug member 34 is breakable from the sleeve member 33 to open the flow path 32 and is thus called a click-tip. As illustrated, a notch 35 is circumferentially formed at the connection between the sleeve member 33 and the plug member 34 to facilitate the breakage of the plug member from the sleeve member.

It will be understood that the flow path control means 31 may be additionally provided in the first section of tubing 26A. In this case, the engagement of the protector 29 A with the hub 29B of the needle 29 need not be fluid tight. That portion 36 of the second section of tubing 26B which encloses the flow path control means 31 has an increased diameter as compared with the remaining portion. Preferably the flow path control means 31 has an outer diameter larger than the inner diameter of the remaining tubing portion. This diameter selection, after the plug member 34 is broken, prevents the plug member 34 from blocking the downstream flow path of the section of tubing 26B or flowing into the blood bag 22B. Entry of the broken plug member 34 into the blood bag is undesirable because it will damage the blood bag during centrifugation. The surrounding portion 36 of an increased diameter may be a tubular member separate from the collecting section of tubing 26B.

The breakable plug member 34 may have a conical shape or truncated shape or a flat tip 37 (FIG. 4) such that the plug member 34, after breakage, may not block the second section of tubing 26B. Further, the plug member 34 is preferably rugged or roughened on the outer surface thereof to prevent the section of tubing 26B, particularly, the surrounding portion 36 from fusing to the plug member 34. Otherwise, when the blood bag is subject to autoclave sterilization or high pressure steam sterilization, the surrounding portion 36 is heat welded to the plug member 34 (this phenomenon is usually called "blocking") and then, the flow path is not fully opened by breaking the flow path control means 31. Surface roughening reduces the contact surface area between the plug member 34 and the surrounding portion 36. Surface roughening may be carried out by any of well-known techniques including embossing, slotting, ribbing and the like. In general, blood bags and tubes are formed of a flexible polyvinyl chloride resin which is liable to "blocking". The flow path control means is preferably formed of a relatively rigid material different from the material of which the bags and tubes are formed, for example, rigid polyvinyl chloride and polycarbonate resins, the polycarbonate resin being most preferred because of easy and complete breakage.

The blood bag system 21 described above is operated as follows when it is applied to plasma exchange therapy.

In collecting blood from the donor, the collecting needle 29 is punctured into the donor's vein. Since the second section of tubing 26B is blocked or closed by the flow path control means 31 at this point, that is, in normal or unbroken state, blood is collected into the first blood bag 22A through the needle 29, main section of tubing 28, and first section of tubing 26A. Thereafter, the first section of tubing 26A is heat sealed over some area, for example, along line X—X in FIG. 3 and then cut intermediate of the sealed area. The first blood bag 22A together with the first section of tubing 26A which is thus separated from the system is placed in a centrifuge where the blood in the bag is centrifuged into plasma and cell components. The thus separated plasma component is then transfused to the patient through the plasma outlet 24 while the cell component is transfused back to the donor through the cell outlet 25, cell return means 30, and needle 29.

Next, the flow path control means 31 in the second section of tubing 26B is manually broken to disconnect the plug member 34 from the sleeve member 33 to place the path 32 in communication with the downstream section of tubing 26B, and blood is collected in the second blood bag 22B through the needle 29 which is kept punctured into the donor's vein. The blood collected in the second blood bag 22B is subjected to the same successive procedures of centrifugation, transfusion and back transfusion as described for the first blood bag 22A.

In the above-described embodiment, during autoclave sterilization with the flow path control means 31 in non-conductive state, the anticoagulant in the first blood bag 22A wets the first section of tubing 26A and the main section of tubing 28 while the anticoagulant in the second blood bag 22B wets the second section of tubing 26B. This permits the blood bags 22A and 22B to be filled with a substantially equal volume of anticoagulant. Since the flow paths to be wetted with the anticoagulant in the blood bags A and 22B are not too long, the anticoagulant may be properly distributed over the respective flow paths.

Since the plug member 34 of the flow path control means 31 which is to be disconnected from the annular base 33 is located in the section of tubing 26B downstream of the annular base 33 with respect to the flow of blood being collected, there is no likelihood that the broken plug member 34 is entrained by the collecting blood flow toward the annular base 33 to again close the flow path 32. This ensures steady blood collection.

The flow path control means 31 may be readily joined to the section of tubing 26B, for example, by heat welding or adhesion, resulting in increased productivity. If that end of the second section of tubing 26B which is remote from the second blood bag 22B is joined to the sleeve member 33 of the flow path control means 31 at a position shown by line Y—Y in FIG. 4, a subassembly of the first blood bag 22 A and the first section of tubing 26A may be identical with a subassembly of the second blood bag 22B and the second section of tubing 26B with the benefit of further improved productivity.

Since the flow path control means 31 is readily breakable irrespective of being enclosed in the section of tubing, ease of operation and safety in service are improved over the prior art systems using a bead or plug.

The flow path control means 31 is located adjacent the cell return means 30 and thus actually placed nearer to the donor and hence, at a relatively high level above the floor. The operator need not squat down for breaking.

Although the flow path control means 31 is provided solely in the second section of tubing 26B in the above-described embodiment, an additional flow path control means may be provided in the first section of tubing 26A.

Although the blood bag system of the present invention is described with respect to the embodiment using two blood bags, the present invention is, of course, applicable to blood bag systems including three or more blood bags.

It is also contemplated that each blood bag is provided with a single transfusion outlet which serves for both plasma and cell transfusion purposes.

In a blood bag system comprising a plurality of blood bags each having an inlet for blood collection and at least one outlet for blood transfusion and containing a given volume of an anticoagulant therein, a corresponding plurality of sections of tubing for blood transfer each having one end connected to the inlet of one blood bag, a main section of tubing having one end connected to the other ends of the sections of tubing in common, a needle connected to the other end of the main section of tubing for collecting blood, and return means connected to the main section of tubing (or any one of the sections of tubing) for returning a cell component of blood, according to the present invention, provided that N is the number of blood bags in the system, flow path control means is positioned in each of sections of tubing corresponding to at least (N−1) blood bags at a point near to the main section of tubing (but on the side of the blood bag with respect to the return means if the return means is connected to the section of tubing), the control means normally blocking or closing fluid communication through the corresponding section of tubing, but when broken, allowing communication through the section of tubing. The volumes of anticoagulant contained in the plurality of blood bags may be substantially equal and properly and uniformly distributed over the sections of tubing and the main section of tubing prior to blood collecting process, offering the advantages of ease of operation and safety in service as well as ease of manufacture.

In one preferred embodiment, the flow path control means comprises an annular base disposed in and sealed to the inner surface of the section of tubing and defining a flow path therethrough, and a plug member integrally connected to that end of the base which is positioned on the side of the blood bag to block the flow path of the base is breakable from the base to open the flow path of the base. With this arrangement, the plug member which is breakable from the base of the flow path control means is located in the blood collecting section of tubing downstream of the base with respect to the collecting blood flow, and there is no likelihood that the broken plug member will be entrained by the collecting blood flow to close the flow path of the base, ensuring steady blood collection.

What we claim is:

1. An autoclave sterilized blood bag system, comprising:
    a first blood bag having an inlet for blood collection and at least one outlet for blood transfusion;
    a second blood bag having an inlet for blood collection and at least one outlet for blood transfusion;
    first and second sections of tubing for blood transfer, each having one end connected to the inlet of said first and second blood bags, respectively;
    a branch pipe including a straight pipe portion, and further including one branch pipe portion and another branch pipe portion each extending angularly from said straight pipe portion and each having an open end;
    a main tube having one end connected to one end of said straight pipe portion of said branch pipe so as to communicate with said other ends of said first and second sections of tubing in common through said branch pipe;
    a needle connected to the other end of said main tube for collecting blood;
    return means for returning a cell component of blood;
    breakable flow path control means positioned in and enclosed by the second section of tubing corresponding to said second blood bag at a point near the branch pipe, said breakable flow path control means blocking fluid communication through the corresponding second section of tubing, but, when broken, allowing fluid communication through said corresponding second section of tubing;
    wherein said straight pipe portion has another end connected to another end of said second section of tubing and extending straight with respect to said main tube and said second section of tubing to the second blood bag at junctions therebetween, the open end of said one branch pipe portion being connected to the other end of the first section of tubing to the first blood bag, and the open end of said another other branch pipe portion being directly connected to said return means; and
    anticoagulant distributed throughout inner surfaces of the blood bags, the first and second sections of tubing, the main tube, the branch pipe, and the needle, which anticoagulant becomes wet during an autoclave sterilization of the whole blood bag system carried out before use.

2. The blood bag system of claim 1, wherein said breakable flow path control means comprises an annular base portion disposed in and sealed to said second section of tubing, and a plug member integrally connected to an end of said base portion which is positioned on the side of said second blood bag, said plug member blocking a flow path through said base portion and having a roughened outer surface, said plug member being breakable apart from said base portion to open said flow path of said base portion.

3. The blood bag system of claim 2, wherein said roughened outer surface of said plug member is embossed to provide said roughening.

4. The blood bag system of claim 2, wherein said roughened outer surface of said plug member has slots therein, to thereby provide said roughening.

5. The blood bag system of claim 2, wherein said roughened outer surface of said plug member has ribs thereon, to thereby provide said roughening.

6. The blood bag system of claim 2, wherein said base portion comprises an annular sleeve, and said plug member comprises a conical plug having a bottom portion connected to said sleeve.

7. The blood bag system of claim 2, wherein said base portion comprises an annular sleeve, and said plug member comprises a flat tip portion.

8. The blood bag system of claim 2, wherein said return means comprises a section of tubing closed with a plug which is puncturable by a hypodermic needle.

9. The blood bag system of claim 1, wherein said needle comprises shield means at the tip thereof for shielding said needle from the outside.

10. The blood bag system of claim 9, wherein said needle comprises a hub at a base portion thereof, and a protector engaged with said hub in a fluid-type manner to enclose the needle therein.

11. The blood bag system of claim 1, wherein said first and second blood bags each having an outlet for transfusion of a plasma component, and another outlet for back transfusion of a cell component of blood.

12. The blood bag system of claim 1, wherein said tubing sections are formed of a flexible polyvinyl chloride resin and wherein said flow path control means is formed of a relatively rigid material different from the material of said tubing sections.

13. The blood bag system of claim 12, wherein said relatively rigid material of which said flow path control means is formed is selected from the group consisting of rigid polyvinyl chloride and polycarbonate.

14. Method for carrying out a plasma transfusion by using the blood bag system of claim 1, comprising the step of:
    puncturing the collecting needle into the donor's vein;
    collecting blood from the donor into the first blood bag through the needle punctured into the donor's vein, the main tube, said straight pipe portion, one branch pipe portion of the branch pipe which is angularly extended with respect to the main tube, and the first section of tubing, with the anticoagulant distributed throughout inner surfaces of the blood bags, the first and second section of tubing, the main tube, the branch pipe, and the needle;

heat sealing over some area of the first section of tubing and cutting said first section of tubing at an intermediate portion of the sealed area to separate the first blood bag from the blood bag system;

placing the separated bag in a centrifuge wherein the blood in the separated bag is centrifuged into plasma and cell components;

transfusing the separated plasma components to the patient through the outlet of the separated bag while the cell components are transfused back to the donor through said outlet, said return means, said another branch pipe portion, said straight pipe portion, said main tube and said needle which is kept punctured into the donor's vein;

manually breaking the flow path control means in the second section of tubing to place the flow path in communication with the second section of tubing;

collecting the blood into the second blood bag through the needle which is kept punctured into the donor's vein, the main tube, the straight pipe portion of the branch pipe which is straight with respect to the main tube and the second section of tubing to the second blood bag at junctions therebetween, and the second section of tubing, the anticoagulant on inner surfaces of the needle, the main tube and the straight pipe portion of the branch pipe having already been lost during the collection of blood into the first blood bag;

heat sealing over some area of the second section of tubing and cutting said section of tubing at an intermediate portion of the sealed area to separate the second blood bag from the blood bag system;

placing the separated second blood bag in a centrifuge where the blood in the separated second blood bag is centrifuged into plasma and cell components;

transfusing the separated plasma components to the patient through the outlet of the separated second blood bag while the cell components are transfused back to the donor through the outlet, return means, said another branch pipe portion, the straight pipe portion, the main tube and needle which is kept punctured into the donor's vein; and removing the needle from the donor's vein.

* * * * *

UNITED STATES PATENT AND TRADEMARK OFFICE
CERTIFICATE OF CORRECTION

PATENT NO. : 4,846,795
DATED : July 11, 1989
INVENTOR(S) : Y. MINAGAWA

It is certified that error appears in the above-identified patent and that said Letters Patent is hereby corrected as shown below:

In the title page, column 2, after "FOREIGN PATENT DOCUMENTS",
insert --OTHER DOCUMENTS
      Introducing Travenol CAPD System II, Travenel
      Nor.J-1067 (1981)--.

Column 4, line 8, "2" should read --21--.

Column 7, line 22, after "base" (in 1st instance), insert --,--.

Column 8, line 61 (claim 14), "step of:" should read
--steps of:--.

Signed and Sealed this

Ninth Day of October, 1990

*Attest:*

HARRY F. MANBECK, JR.

*Attesting Officer*      *Commissioner of Patents and Trademarks*